(12) United States Patent
Ohsawa et al.

(10) Patent No.: US 7,498,126 B2
(45) Date of Patent: Mar. 3, 2009

(54) PHOTOACID GENERATORS, CHEMICALLY AMPLIFIED RESIST COMPOSITIONS, AND PATTERNING PROCESS

(75) Inventors: Youichi Ohsawa, Joetsu (JP); Kazunori Maeda, Joetsu (JP); Satoshi Watanabe, Joetsu (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 77 days.

(21) Appl. No.: 11/806,970

(22) Filed: Jun. 5, 2007

(65) Prior Publication Data

US 2007/0292768 A1 Dec. 20, 2007

(30) Foreign Application Priority Data

Jun. 14, 2006 (JP) ............... 2006-164383

(51) Int. Cl.
*G03C 1/73* (2006.01)
*G03F 7/031* (2006.01)
*G03F 7/039* (2006.01)
*G03F 7/20* (2006.01)
*G03F 7/30* (2006.01)

(52) U.S. Cl. ............ 430/922; 430/919; 430/921; 430/270.1; 430/905; 430/325; 430/326; 430/330; 564/254; 549/68; 549/78; 549/80; 558/408

(58) Field of Classification Search ............... None
See application file for complete search history.

(56) References Cited

U.S. PATENT DOCUMENTS

| | | | |
|---|---|---|---|
| 6,004,724 A | 12/1999 | Yamato et al. | |
| 6,136,502 A | 10/2000 | Satoshi et al. | |
| 6,261,738 B1 | 7/2001 | Asakura et al. | |
| 6,512,020 B1 | 1/2003 | Asakura et al. | |
| 6,743,562 B2 | 6/2004 | Momota et al. | |
| 6,746,817 B2 | 6/2004 | Takeda et al. | |
| 6,835,804 B2 | 12/2004 | Takeda et al. | |
| 6,949,323 B2 | 9/2005 | Takeda et al. | |
| 2004/0260031 A1 | 12/2004 | Takeda et al. | |

FOREIGN PATENT DOCUMENTS

| | | |
|---|---|---|
| GB | 2348644 A | 10/2000 |
| JP | 9-95479 A | 4/1997 |
| JP | 9-208554 A | 8/1997 |
| JP | 9-230588 A | 9/1997 |
| JP | 9-301948 A | 11/1997 |
| JP | 2906999 B2 | 4/1999 |
| JP | 11-190904 A | 7/1999 |
| JP | 2000-314956 A | 11/2000 |
| JP | 2002-508774 A | 3/2002 |
| JP | 2002-202603 A | 7/2002 |
| JP | 2002-202610 A | 7/2002 |
| JP | 2002-234910 A | 8/2002 |
| JP | 2002-278053 A | 9/2002 |
| JP | 2003-84440 A | 3/2003 |
| JP | 2003-131384 A | 5/2003 |
| JP | 2003-307840 A | 10/2003 |
| JP | 2004-8766 A | 1/2004 |
| JP | 2004-348014 A | 12/2004 |
| JP | 2005-8766 A | 1/2005 |
| JP | 2005-8769 A | 1/2005 |
| WO | WO-2004/074242 A3 | 9/2004 |

OTHER PUBLICATIONS

Asakura et al ("Novel Photoacid Generators for Chemically Amplified Resists with g-line, i-line and DUV Exposure", Proceedings of SPIE, vol. 4345 (2001), p. 484-493.*

Koji Arimitsu et al. "Effect of Phenolic Hydroxyl Residues on the Improvement of Acid-Proliferation-Type Photoimaging Materials," Journal of Photopolymer Science and Technology, vol. 9, No. 1(1996) pp. 29-30.

Koji Arimitsu et al. "Sensitivity Enhancement of Chemical-Amplification-Type Photoimaging Materials by Acetoacetic Acid Derivatives," Journal of Photopolymer Science and Technology, vol. 8, No. 1(1995) pp. 43-44.

Kazuaki Kudo et al. "Enhancement of the Sensetivety of Chemical-Amplification-Type Photoimaging Materials by b-Tosyloxyketone Acetals," Journal of Photopolymer Science and Technology vol. 8, No. 1(1995) pp. 45-46.

* cited by examiner

*Primary Examiner*—Sin J. Lee
(74) *Attorney, Agent, or Firm*—Birch, Stewart, Kolasch & Birch, LLP

(57) ABSTRACT

A photoacid generator has formula (1). A chemically amplified resist composition comprising the photoacid generator has advantages including a high resolution, focus latitude, long-term PED dimensional stability, and a satisfactory pattern profile shape. When the photoacid generator is combined with a resin having acid labile groups other than those of the acetal type, resolution and top loss are improved. The composition is suited for deep UV lithography.

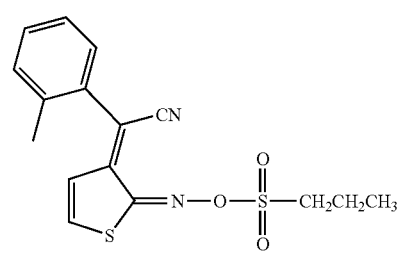

(1)

17 Claims, No Drawings

PHOTOACID GENERATORS, CHEMICALLY AMPLIFIED RESIST COMPOSITIONS, AND PATTERNING PROCESS

CROSS-REFERENCE TO RELATED APPLICATION

This non-provisional application claims priority under 35 U.S.C. §119(a) on Patent Application No. 2006-164383 filed in Japan on Jun. 14, 2006, the entire contents of which are hereby incorporated by reference.

TECHNICAL FIELD

This invention relates to photoacid generators for chemically amplified resist compositions, chemically amplified resist compositions comprising the photoacid generators, and a patterning process using the same. The chemically amplified resist compositions are sensitive to such radiation as UV, deep UV, electron beams, x-rays, excimer laser beams, γ-rays, and synchrotron radiation and suitable for the microfabrication of integrated circuits.

BACKGROUND OF THE INVENTION

While a number of efforts are currently being made to achieve a finer pattern rule in the drive for higher integration and operating speeds in LSI devices, deep-ultraviolet lithography is thought to hold particular promise as the next generation in microfabrication technology.

One technology that has attracted a good deal of attention recently utilizes as the deep UV light source a high-intensity KrF excimer laser and an ArF excimer laser of a shorter wavelength. There is a desire to have a microfabrication technique of finer definition by combining exposure light of shorter wavelength with a resist material having a higher resolution.

In this regard, the recently developed, acid-catalyzed, chemical amplification type resist materials are expected to comply with the deep UV lithography because of their many advantages including high sensitivity, resolution and dry etching resistance. The chemically amplified resist materials include positive working materials that leave the unexposed areas with the exposed areas removed and negative working materials that leave the exposed areas with the unexposed areas removed.

In a chemically amplified positive resist composition to be developed with an alkaline developer, a resin and/or compound in which an alkali-soluble phenol or carboxylic acid is partially or entirely protected with acid labile protective groups (commonly referred to as "acid labile groups") is catalytically decomposed with the acid generated upon exposure, to generate the phenol or carboxylic acid in exposed areas, whereupon the exposed areas are removed with the alkaline developer. In a similar negative resist composition, a resin and/or compound having an alkali-soluble phenol or carboxylic acid and a compound capable of bonding or crosslinking said resin or compound under the action of an acid (referred to as "acid crosslinker") are crosslinked with the acid generated upon exposure, to render exposed areas insoluble in an alkaline developer, whereupon unexposed areas are removed with the alkaline developer.

On use of the chemically amplified positive resist composition, a resist film is formed by dissolving a resin having acid labile groups as a binder and a compound capable of generating an acid upon exposure to radiation (referred to as "photoacid generator") in a solvent, applying the resist solution onto a substrate by a variety of methods, and evaporating off the solvent optionally by heating. The resist film is then exposed to radiation, for example, deep UV through a mask of a predetermined pattern. This is optionally followed by post-exposure baking (PEB) for promoting acid-catalyzed reaction. The exposed resist film is developed with an aqueous alkaline developer for removing the exposed areas of the resist film, obtaining a positive pattern profile. The substrate is then etched by any desired technique. Finally the remaining resist film is removed by dissolution in a remover solution or ashing, leaving the substrate having the desired pattern profile.

The chemically amplified positive resist composition adapted for KrF excimer lasers generally uses a phenolic resin, for example, polyhydroxystyrene in which some or all of the hydrogen atoms of phenolic hydroxyl groups are protected with acid labile protective groups. Iodonium salts, sulfonium salts, bissulfonyldiazomethane compounds, N-sulfonyloxydicarboximide compounds and O-arylsulfonyloxime compounds are typically used as the photoacid generator. If necessary, there are added additives, for example, a dissolution inhibiting or promoting compound in the form of a carboxylic acid and/or phenol derivative having a molecular weight of up to 3,000 in which some or all of the hydrogen atoms of carboxylic acid and/or phenolic hydroxyl groups are protected with acid labile groups, a carboxylic acid compound for improving dissolution characteristics, a basic compound for improving contrast, and a surfactant for improving coating characteristics.

U.S. Pat. No. 6,004,724 (or corresponding JP-A 2002-508774) discloses the photoacid generators in the form of O-alkanesulfonyloxime compounds as shown below. They have a satisfactory sensitivity and resolution and are free of such drawbacks as poor compatibility with resins and low solubility in resist solvents as found with other photoacid generators like sulfonium salts and iodonium salts. They are advantageously used as the photoacid generators in chemically amplified resist compositions, especially chemically amplified positive resist compositions adapted for KrF excimer laser. JP-A 2002-202603 describes a wide spectrum of photoacid generators and discloses that by combining resins having acid labile groups, typically acetal groups, with these photoacid generators, improvements in nano-order edge roughness and the footing of resist pattern on silicon nitride substrates are achievable. JP-A 2003-307840 discloses that by combining resins having acid labile groups, typically acetal groups, with oximesulfonate photoacid generators, improvements in line edge roughness on organic antireflective coatings and PED stability are achievable.

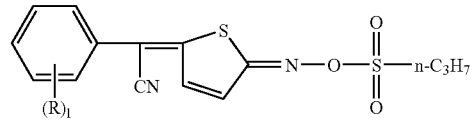

As the requisite pattern size is reduced, however, there arise problems. For example, even the use of resist compositions having these photoacid generators combined with the existing acid labile group-bearing resins encounters the problem of poor resolution. In the step where low reflectance substrates such as organic antireflective coatings cannot be used, for example, ion implantation and other steps where resist patterns are formed on inorganic substrates such as silicon, silicon nitride, titanium nitride, silicon oxide substrates and inorganic nitride films, even the use of resist compositions having these photoacid generators combined with the existing acid labile group-bearing resins encounters the problem that the influence of standing waves by substrate reflection or the influence of contamination from the inorganic substrates prevents formation of satisfactory pattern profiles.

Particularly when different species of materials are present on an inorganic substrate, for example, when plural species of materials having different electric properties, like silicon nitride and silicon, are present within a common plane because of device design considerations, the reflectance or the degree of contamination from the substrate shows local variations. Accordingly, in order to form a pattern from a single resist material, there exists a need for a material which is less sensitive to reflectance or contamination from the substrate.

For resolution improvement, it is a practice to use more acid labile groups, typically more acid labile acetal groups. However, the reduction of pattern size invites a tendency of reducing the thickness of resist film as well. When a phenolic resin having acid labile groups of acetal type is used, the resist surface becomes more dissolvable. The dissolution of the resist pattern at the top raises problems including a top loss that the pattern profile shape is rounded at the top. The remaining resist pattern becomes thinner, making it impossible to secure a film thickness sufficient for the etching or ion implantation step.

When the resist is applied onto inorganic substrates such as SiON substrates which are highly reflective substrates, there arises a problem that standing waves prevent formation of a satisfactory pattern shape. One approach for avoiding these problems is to use resins having acid labile groups of tertiary ether or tertiary ester type which are less labile than the acid labile groups of acetal type (see JP-A 2005-8766). This approach is successful in reducing the top loss, but fails to overcome the problems of micro-pattern rectangularity, footing and standing waves, and is low in resolution.

The photoacid generator for use in resist compositions is required to have a fully high solubility (or compatibility) in resist solvents and resins, good storage stability, non-toxicity, ease of application, pattern profile shape, PED stability, high resolution, wide focal depth, and high sensitivity. The O-arene or alkanesulfonyloxime compound photoacid generators and resist compositions comprising the same do not satisfy all these requirements, especially with regard to the pattern profile shape on inorganic substrates.

In the recent stage when the pattern feature of integrated circuits becomes more miniaturized, more stringent requirements are imposed on the problem of pattern profile shape accompanied with a resist thickness reduction.

DISCLOSURE OF THE INVENTION

An object of the invention is to provide a photoacid generator used to formulate a chemically amplified resist composition which is improved in pattern profile shape particularly when the thickness of resist film is reduced; a resist composition comprising the same; and a patterning process.

We have found that a chemically amplified resist composition comprising an O-propanesulfonyloxime compound of the general formula (1), shown below, possesses a number of great advantages including dissolution, storage stability, effective coating, minimized line width variation or shape degradation during long-term PED, good pattern profile shape particularly at reduced film thickness, and a high resolution enough for microfabrication, particularly when processed by deep UV lithography.

The present invention provides a photoacid generator, a chemically amplified resist composition comprising the same, and a patterning process, as defined below.

In a first aspect, the invention provides a photoacid generator for use in chemically amplified resist compositions, having the formula (1).

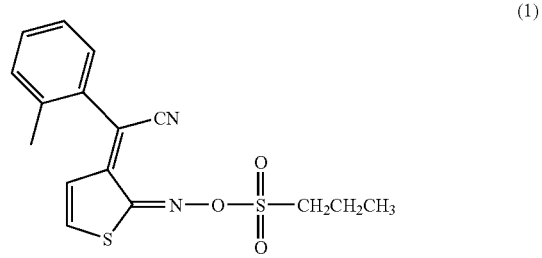

In a second aspect, the invention provides a chemically amplified resist composition, specifically a chemically amplified positive resist composition, comprising (A) a resin which changes its solubility in an alkaline developer under the action of an acid, and (B) the photoacid generator of formula (1).

In a third aspect, the invention provides a process for forming a pattern, comprising the steps of (i) applying the resist composition onto a substrate to form a coating, (ii) heat treating the coating and exposing the coating to high energy radiation with a wavelength of up to 300 nm or electron beam through a photomask, (iii) optionally heat treating the exposed coating, and developing the coating with a developer. The substrate is typically an inorganic substrate, preferably a SiON film. Preferably the coating of the resist composition on the inorganic substrate has a thickness equal to or less than 0.4 μm.

BENEFITS OF THE INVENTION

The chemically amplified resist composition comprising a photoacid generator capable of generating an acid upon exposure to actinic radiation according to the invention has many advantages including dissolution, focus latitude, minimized line width variation or shape degradation even on long-term PED, a satisfactory pattern profile shape after development, and a high resolution enough for microfabrication. Particularly when the photoacid generator is combined with a resin having acid labile groups other than those of the acetal type, a high resolution is achieved and the resist shape is improved because the dissolution of resist film top portion in unexposed areas is restrained. The composition is thus suited for microfabrication, especially by deep UV lithography.

DESCRIPTION OF THE PREFERRED EMBODIMENTS

Photoacid Generator

In the first embodiment, the invention provides a photoacid generator having the formula (1) for use in chemically amplified resist compositions.

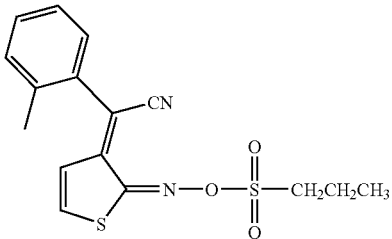

(1)

The compound of formula (1) has an oxime skeleton which can be synthesized by reacting a substituted phenylacetonitrile compound with 2-nitrothiophene in an alcohol solvent under basic conditions.

The target O-sulfonyloxime compound is preferably prepared by dissolving an oxime compound and a corresponding propanesulfonyl chloride or propanesulfonic acid anhydride in a solvent such as tetrahydrofuran (THF) or $CH_2Cl_2$, and effecting reaction under basic conditions. Also preferably, the reaction may be effected in a basic solvent such as pyridine.

Resist Composition

In the second embodiment, the present invention provides a chemically amplified resist composition comprising a photoacid generator of the formula (1), the composition being sensitive to such radiation as ultraviolet radiation, deep ultraviolet radiation, electron beams, x-rays, excimer laser beams, gamma-rays or synchrotron radiation and suitable for the microfabrication of integrated circuits. The resist composition may be either positive or negative. From the standpoint of resolution and the like, positive resist compositions are more preferred.

The resist compositions of the invention include a variety of embodiments:

1) a chemically amplified positive working resist composition comprising (A) a resin which changes its solubility in an alkaline developer under the action of an acid, (B) the photoacid generator of formula (1), and (F) an organic solvent;

2) a chemically amplified positive resist composition of 1) further comprising (C) a photoacid generator capable of generating an acid upon exposure to radiation other than component (B);

3) a chemically amplified positive resist composition of 1) or 2) further comprising (D) a basic compound;

4) a chemically amplified positive resist composition of 1) to 3) further comprising (E) an organic acid derivative; and 5) a chemically amplified positive resist composition of 1) to 4) further comprising (G) a compound with a molecular weight of up to 3,000 which changes its solubility in an alkaline developer under the action of an acid; as well as 6) a chemically amplified negative working resist composition comprising (B) the photoacid generator of formula (1), (F) an organic solvent, (H) an alkali-soluble resin, and (I) an acid crosslinker which forms a crosslinked structure under the action of an acid;

7) a chemically amplified negative resist composition of 6) further comprising the above component (C);

8) a chemically amplified negative resist composition of 6) or 7) further comprising the above component (D); and 9) a chemically amplified negative resist composition of 6) to 8) further comprising (J) an alkali-soluble compound having a molecular weight of up to 2,500; but not limited thereto.

Now the respective components are described in detail.

Component (A)

Component (A) is a resin which changes its solubility in an alkaline developer solution under the action of an acid. In the case of chemically amplified positive resist compositions, it is preferably, though not limited thereto, an alkali-soluble resin having phenolic hydroxyl and/or carboxyl groups in which some or all of the phenolic hydroxyl and/or carboxyl groups are protected with acid-labile protective groups having a C—O—C linkage.

The alkali-soluble resins having phenolic hydroxyl and/or carboxyl groups include homopolymers and copolymers of p-hydroxystyrene, m-hydroxystyrene, α-methyl-p-hydroxystyrene, 4-hydroxy-2-methylstyrene, 4-hydroxy-3-methylstyrene, hydroxyindene, 4-vinylbenzoic acid, methacrylic acid and acrylic acid, and such copolymers having a carboxylic derivative or diphenyl ethylene introduced at their terminus.

Also included are copolymers in which other units are introduced in addition to the above-described units in such a proportion that the solubility in an alkaline developer may not be extremely reduced. Suitable other units are units free of alkali-soluble sites such as units derived from styrene, α-methylstyrene, acrylate, methacrylate, hydrogenated hydroxystyrene, maleic anhydride, maleimide, and substituted or unsubstituted indene. Substituents on the acrylates and methacrylates may be any of the substituents which do not undergo acidolysis. Exemplary substituents are straight, branched or cyclic $C_{1-8}$ alkyl groups and aromatic groups such as aryl groups, but not limited thereto.

Examples of the alkali-soluble resins or polymers are given below. They may be used as the raw material for the resin (A) which changes its solubility in an alkaline developer solution under the action of an acid or as the alkali-soluble resin (H). Examples include poly(p-hydroxystyrene), poly(m-hydroxystyrene), poly(4-hydroxy-2-methylstyrene), poly(4-hydroxy-3-methylstyrene), poly(α-methyl-p-hydroxystyrene), partially hydrogenated p-hydroxystyrene copolymers, p-hydroxystyrene-α-methyl-p-hydroxystyrene copolymers, p-hydroxystyrene-α-methylstyrene copolymers, p-hydroxystyrene-styrene copolymers, p-hydroxystyrene-m-hydroxystyrene copolymers, p-hydroxystyrene-indene copolymers, p-hydroxystyrene-acrylic acid copolymers, p-hydroxystyrene-methacrylic acid copolymers, p-hydroxystyrene-methyl acrylate copolymers, p-hydroxystyrene-acrylic acid-methyl methacrylate copolymers, p-hydroxystyrene-methyl methacrylate copolymers, p-hydroxystyrene-methacrylic acid-methyl methacrylate copolymers, poly(methacrylic acid), poly(acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers, but are not limited to these combinations.

Preferred are poly(p-hydroxystyrene), partially hydrogenated p-hydroxystyrene copolymers, p-hydroxystyrene-styrene copolymers, p-hydroxystyrene-indene copolymers, p-hydroxystyrene-p-vinylbenzoic acid copolymers, p-hydroxystyrene-acrylic acid copolymers, and p-hydroxystyrene-methacrylic acid copolymers.

Examples of the resin which changes its solubility in an alkaline developer under the action of an acid as component (A) include polymers or high molecular weight compounds comprising recurring units of the following general formula (2a), (2a'), (2a") or (2a''').

One preferred embodiment is a polymer comprising recurring units of the following general formula (2a) wherein the polymer contains units in which hydrogen atoms of phenolic hydroxyl groups are partially substituted with acid labile groups of one or more types, a proportion of the acid labile group-bearing units is on the average from more than 0 mol % to 80 mol % based on the entire polymer, and the polymer has a weight average molecular weight of 3,000 to 100,000. It is noted that the weight average molecular weight (Mw) is as measured by gel permeation chromatography (GPC) versus polystyrene standards.

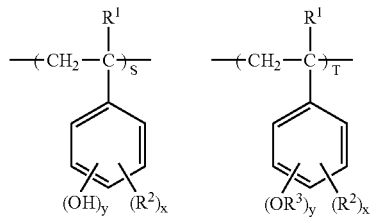

(2a)

Herein $R^1$ is hydrogen or methyl, $R^2$ is a straight, branched or cyclic alkyl group of 1 to 8 carbon atoms, x is 0 or a positive integer, y is a positive integer, satisfying $x+y \leq 5$, $R^3$ is an acid labile group, S and T are positive integers, satisfying $0<T/(S+T) \leq 0.8$.

Another preferred embodiment is a polymer comprising recurring units of the following general formula (2a') wherein the polymer contains on the average from more than 0 mol % to 50 mol % of those units derived from acrylate and methacrylate, and also contains on the average from more than 0 mol % to 80 mol % of acid labile group-bearing units, based on the entire recurring units of the polymer, and the polymer has a weight average molecular weight of 3,000 to 100,000.

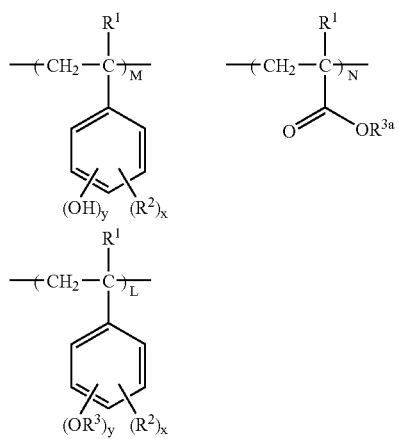

(2a')

Herein $R^1$ is hydrogen or methyl, $R^2$ is a straight, branched or cyclic alkyl group of 1 to 8 carbon atoms, $R^3$ is an acid labile group, $R^{3a}$ is hydrogen or an acid labile group, at least some of $R^{3a}$ being acid labile groups, x is 0 or a positive integer, y is a positive integer, satisfying $x+y \leq 5$, M and N are positive integers, L is 0 or a positive integer, satisfying $0<N/(M+N+L) \leq 0.5$ and $0<(N+L)/(M+N+L) \leq 0.8$.

A further preferred embodiment is a polymer comprising recurring units of the following general formula (2a'') wherein the polymer contains on the average from more than 0 mol % to 50 mol % of those units derived from indene and/or substituted indene, and also contains on the average from more than 0 mol % to 80 mol % of acid labile group-bearing units, based on the entire recurring units of the polymer, and the polymer has a weight average molecular weight of 3,000 to 100,000.

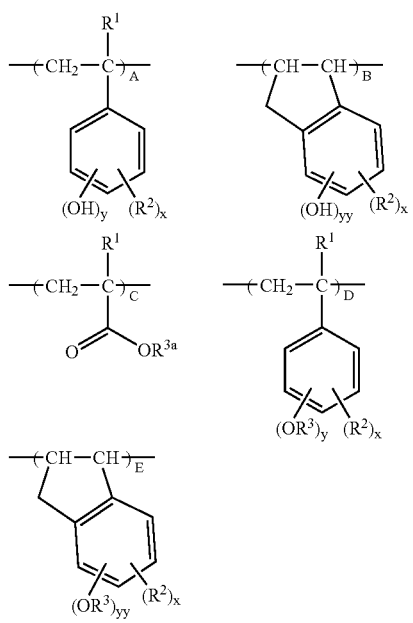

(2a'')

Herein $R^1$ is hydrogen or methyl, $R^2$ is a straight, branched or cyclic alkyl group of 1 to 8 carbon atoms, $R^3$ is an acid labile group, $R^{3a}$ is hydrogen or an acid labile group, at least some of $R^{3a}$ being acid labile groups, x is 0 or a positive integer, y is a positive integer, satisfying $x+y \leq 5$, yy is 0 or a positive integer, satisfying $x+yy \leq 4$, A and B are positive integers, C, D and E each are 0 or a positive integer, satisfying $0<(B+E)/(A+B+C+D+E) \leq 0.5$ and $0<(C+D+E)/(A+B+C+D+E) \leq 0.8$.

A still further preferred embodiment is a polymer comprising recurring units of the following general formula (2a''') wherein the polymer contains on the average from more than 0 mol % to 50 mol % of those units derived from tertiary alkoxycarbonylstyrene, and also contains on the average from more than 0 mol % to 80 mol % of acid labile group-bearing units, based on the entire recurring units of the polymer, and the polymer has a weight average molecular weight of 3,000 to 100,000.

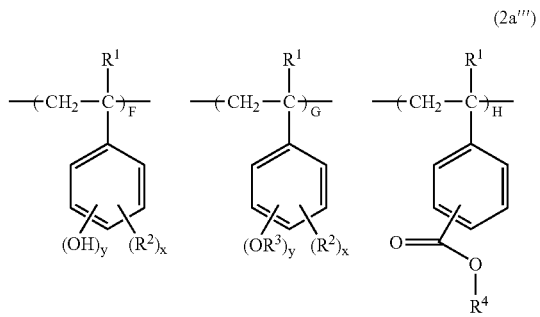

(2a''')

Herein $R^1$ is hydrogen or methyl, $R^2$ is a straight, branched or cyclic alkyl group of 1 to 8 carbon atoms, $R^3$ is an acid labile group, $R^4$ is a tertiary alkyl group of 4 to 20 carbon atoms, x is 0 or a positive integer, y is a positive integer, satisfying x+y≦5, F and H are positive integers, G is 0 or a positive integer, satisfying 0<H/(F+G+H)≦0.5 and 0<(G+H)/(F+G+H)≦0.8.

In the event some of phenolic hydroxyl groups or some or all of carboxyl groups on the alkali-soluble resin are protected with acid labile substituent groups represented by C—O—C linkage, the acid labile groups are selected from a variety of such groups. The preferred acid labile groups are groups of the following general formulae (3) to (6), tertiary alkyl groups of 4 to 20 carbon atoms, preferably 4 to 15 carbon atoms, trialkylsilyl groups whose alkyl groups each have 1 to 6 carbon atoms, oxoalkyl groups of 4 to 20 carbon atoms, or aryl-substituted alkyl groups of 7 to 20 carbon atoms. Inter alia, groups of the general formula (5) and (6) and tertiary alkyl groups of 4 to 20 carbon atoms, especially 4 to 15 carbon atoms are more preferred.

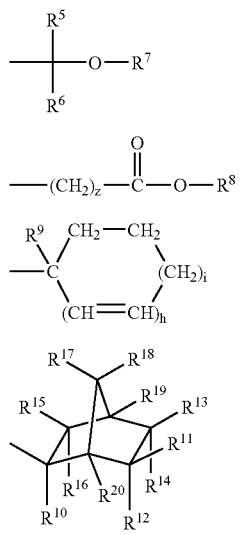

Herein $R^5$ and $R^6$ are independently hydrogen or straight, branched or cyclic alkyl groups of 1 to 18 carbon atoms, preferably 1 to 10 carbon atoms, for example, methyl, ethyl, propyl, isopropyl, n-butyl, sec-butyl, tert-butyl, cyclopentyl, cyclohexyl, 2-ethylhexyl and n-octyl. $R^7$ is a monovalent hydrocarbon group of 1 to 18 carbon atoms, preferably 1 to 10 carbon atoms, which may have a hetero atom (e.g., oxygen atom), for example, straight, branched or cyclic alkyl groups, and such groups in which some hydrogen atoms are substituted by hydroxyl, alkoxy, oxo, amino or alkylamino groups. Illustrative examples of the substituted alkyl groups are given below.

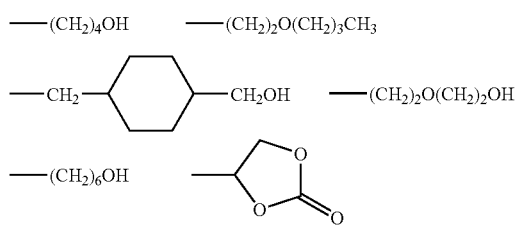

A pair of $R^5$ and $R^6$, a pair of $R^5$ and $R^7$, or a pair of $R^6$ and $R^7$, taken together, may form a ring. Each of $R^5$, $R^6$ and $R^7$ is a straight or branched alkylene group of 1 to 18 carbon atoms, preferably 1 to 10 carbon atoms, when they form a ring.

$R^8$ is a tertiary alkyl group of 4 to 20 carbon atoms, preferably 4 to 15 carbon atoms, a trialkylsilyl group whose alkyl groups each have 1 to 6 carbon atoms, an oxoalkyl group of 4 to 20 carbon atoms or a group of formula (3). Exemplary tertiary alkyl groups are tert-butyl, tert-amyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, 2-ethyl-2-adamantyl and 1-adamantyl-1-methylethyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-5-oxooxolan-4-yl. Letter z is an integer of 0 to 6.

$R^9$ is a straight, branched or cyclic alkyl group of 1 to 8 carbon atoms or substituted or unsubstituted aryl group of 6 to 20 carbon atoms. Exemplary straight, branched or cyclic alkyl groups include methyl, ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl and cyclohexylethyl. Exemplary substituted or unsubstituted aryl groups include phenyl, methylphenyl, naphthyl, anthryl, phenanthryl, and pyrenyl. Letter h is equal to 0 or 1, i is equal to 0, 1, 2 or 3, satisfying 2h+i=2 or 3.

$R^{10}$ is a straight, branched or cyclic alkyl group of 1 to 8 carbon atoms or substituted or unsubstituted aryl group of 6 to 20 carbon atoms, examples of which are as exemplified for $R^9$. $R^{11}$ to $R^{20}$ are independently hydrogen or monovalent hydrocarbon groups of 1 to 15 carbon atoms which may contain a hetero atom, for example, straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl, and cyclohexylbutyl, and substituted forms of the foregoing groups in which some hydrogen atoms are substituted by hydroxyl, alkoxy, carboxy, alkoxycarbonyl, oxo, amino, alkylamino, cyano, mercapto, alkylthio, and sulfo groups. Any two of $R^{11}$ to $R^{20}$, for example, a pair of $R^{11}$ and $R^{12}$, a pair of $R^{11}$ and $R^{13}$, a pair of $R^{12}$ and $R^{14}$, a pair of $R^{13}$ and $R^{14}$, a pair of $R^{15}$ and $R^{16}$, or a pair of $R^{17}$ and $R^{18}$, taken together, may form a ring. When any two of $R^{11}$ to $R^{20}$ form a ring, each is a divalent hydrocarbon group of 1 to 15 carbon atoms which may contain a hetero atom, examples of which are the above-exemplified monovalent hydrocarbon groups with one hydrogen atom eliminated. Also, two of $R^{11}$ to $R^{20}$ which are attached to adjacent carbon atoms (for example, a pair of $R^{11}$ and $R^{13}$, a pair of $R^{13}$ and $R^{19}$, or a pair of $R^{17}$ and $R^{19}$) may directly bond together to form a double bond.

Of the acid labile groups of formula (3), illustrative examples of the straight or branched groups are given below.

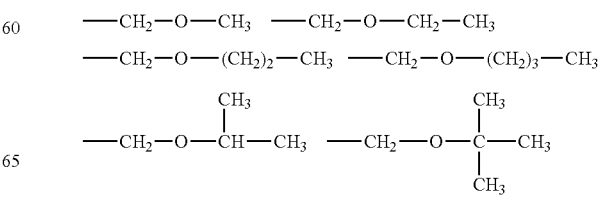

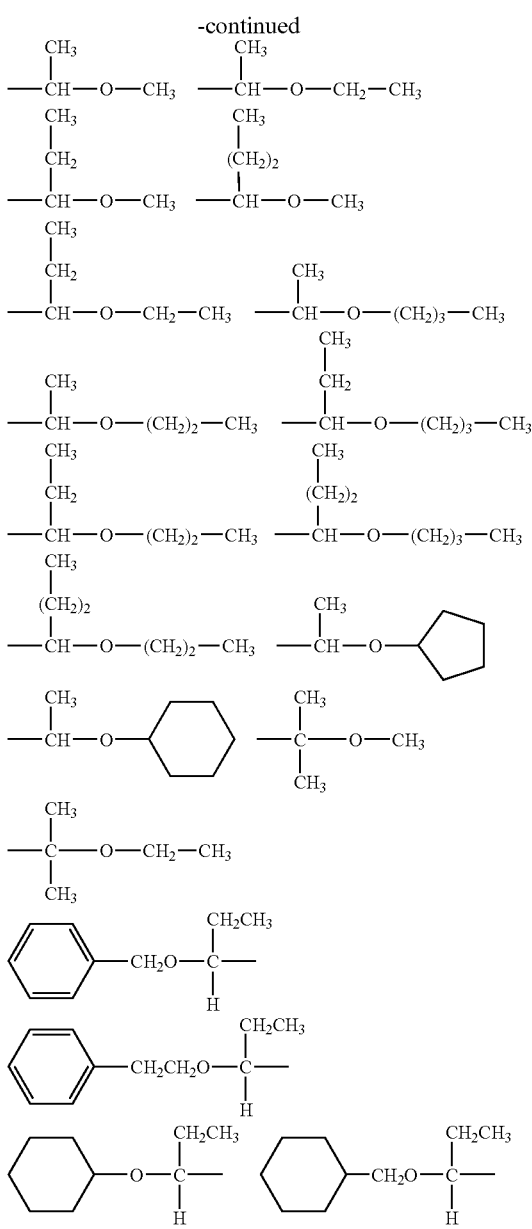

Also included are 1-methoxy-2-methylpropyl, 1-ethoxy-2-methylpropyl, and 1-propoxy-2-methylpropyl groups, which are described in JP-A 2004-348014.

Of the acid labile groups of formula (3), illustrative examples of the cyclic groups include tetrahydrofuran-2-yl, 2-methyltetrahydrofuran-2-yl, tetrahydropyran-2-yl and 2-methyltetrahydropyran-2-yl.

Illustrative examples of the acid labile groups of formula (4) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Illustrative examples of the acid labile groups of formula (5) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, 3-ethyl-1-cyclohexen-3-yl, and 1-cyclohexyl-cyclopentyl.

Illustrative examples of the acid labile groups of formula (6) are given below.

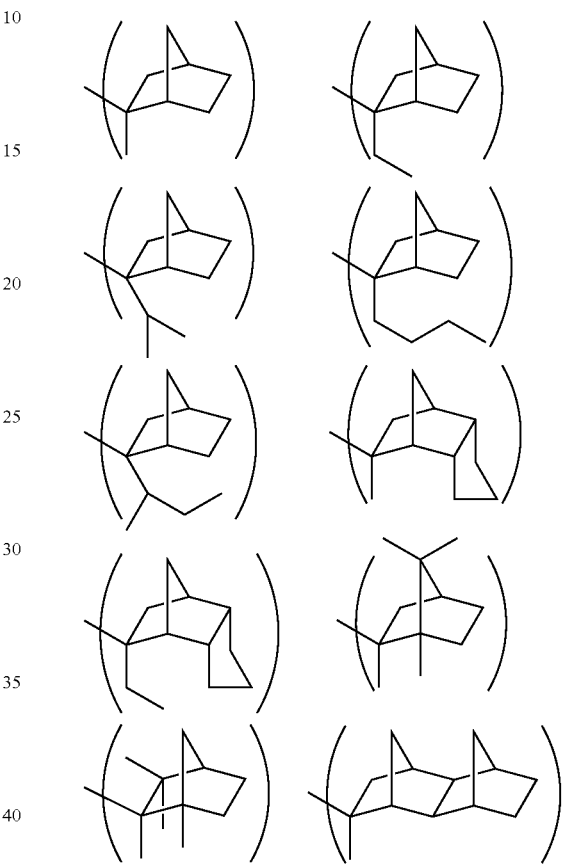

Exemplary of the tertiary alkyl group of 4 to 20 carbon atoms, preferably 4 to 15 carbon atoms, are tert-butyl, tert-amyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, 2-ethyl-2-adamantyl, 1-adamantyl-1-methyl-ethyl.

Exemplary of the trialkylsilyl groups whose alkyl groups each have 1 to 6 carbon atoms are trimethylsilyl, triethylsilyl, and tert-butyldimethylsilyl.

Exemplary of the oxoalkyl groups of 4 to 20 carbon atoms are 3-oxocyclohexyl and groups represented by the following formulae.

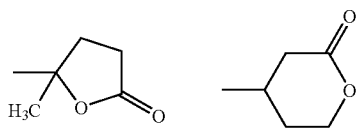

Exemplary of the aryl-substituted alkyl groups of 7 to 20 carbon atoms are benzyl, methylbenzyl, dimethylbenzyl, diphenylmethyl, and 1,1-diphenylethyl.

For the synthesis of polymers of formula (2a'), reference may be made to JP-A 2002-234910 and JP-A 2003-131384. For the synthesis of polymers of formula (2a"), reference may be made to JP-A 2002-202610 and JP-A 2003-84440. For the synthesis of polymers of formula (2a'''), reference may be made to JP-A 2004-8766 and JP-A 2005-8769.

In the chemically amplified positive resist composition of the invention, the resin used as component (A) is as described above while the preferred acid labile groups to be substituted for phenolic hydroxyl groups are tert-butyl and tert-amyl. Also preferably, the hydrogen atoms of carboxyl groups on vinylbenzoic acid units and the hydrogen atoms of carboxyl groups on methacrylic acid or acrylic acid are protected with substituent groups as typified by tert-butyl, tert-amyl, 2-methyl-2-adamantyl, 2-ethyl-2-adamantyl, 1-(1-adamantyl)-1-methyl-ethyl, 1-ethylcyclopentyl, 1-ethylcyclohexyl, 1-cyclohexylcyclopentyl, and 1-ethylnorbornyl.

In a single polymer, these substituents may be incorporated alone or in admixture of two or more types. A blend of two or more polymers having substituents of different types is also acceptable.

The percent proportion of these substituents substituting for phenol and carboxyl groups in the polymer is not critical. Preferably the percent substitution is selected such that when a resist composition comprising the polymer is applied onto a substrate to form a coating, the unexposed area of the coating may have a dissolution rate of 0.01 to 10 Å/sec in a 2.38% tetramethylammonium hydroxide (TMAH) developer.

On use of a polymer containing a greater proportion of carboxyl groups which can reduce the alkali dissolution rate, the percent substitution must be increased or non-acid-decomposable substituents to be described later must be introduced.

To impart a certain function, suitable substituent groups may be introduced into some of the phenolic hydroxyl and carboxyl groups on the acid labile group-protected polymer. Exemplary are substituent groups for improving adhesion to the substrate, non-acid-labile groups for adjusting dissolution in an alkali developer, and substituent groups for improving etching resistance. Illustrative, non-limiting, substituent groups include 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxolanyl, 4-methyl-2-oxo-4-oxanyl, methyl, ethyl, propyl, n-butyl, sec-butyl, acetyl, pivaloyl, adamantyl, isoboronyl, and cyclohexyl.

For the purpose of minimizing the influence of standing waves due to reflected waves on highly reflective substrates, substituent groups or resin units which are effective for reducing the transmittance at the exposure wavelength may be introduced. For example, tert-butyl 4-vinylbenzoate and tert-amyl 4-vinylbenzoate may advantageously be used because they have both the role of acid labile group and the function of transmittance control.

In the resist composition of the invention, the resin used may be of a single type or a mixture of two or more types. When more than one type of resin is used, it is preferred that at least one type be a resin free of acid labile groups of the acetal type.

In the resist composition of the invention, the above-described resin is added in any desired amount, and usually 65 to 99 parts by weight, preferably 65 to 98 parts by weight among 100 parts by weight of the solids in the composition. The term "solids" is used to encompass all components in the resist composition excluding the solvent.

With respect to component (B), illustrative examples of the photoacid generators of formulae (1) are as described above.

In the chemically amplified resist composition, an appropriate amount of the photoacid generator added is from 0.1 part to 10 parts by weight, and preferably from 1 to 5 parts by weight, among 100 parts by weight of the solids in the composition. A less amount of the photoacid generator below the range fails to generate a sufficient amount of acid to deprotect acid labile groups in the polymer. Too large amounts may excessively reduce the transmittance of resist film, failing to form a rectangular pattern, and give rise to problems of abnormal particles and deposits during resist storage. The photoacid generators may be used alone or in admixture of two or more.

Component (C)

In one preferred embodiment, the resist composition further contains (C) a compound capable of generating an acid upon exposure to high-energy radiation (UV, deep UV, electron beams, x-rays, excimer laser beams, gamma-rays or synchrotron radiation), that is, a second photoacid generator other than component (B). Suitable second photoacid generators include sulfonium salts, iodonium salts, sulfonyldiazomethane and N-sulfonyloxydicarboximide photoacid generators. Exemplary second photoacid generators are given below while they may be used alone or in admixture of two or more.

Sulfonium salts are salts of sulfonium cations with sulfonates, bis(substituted alkylsulfonyl)imides and tris(substituted alkylsulfonyl)methides. Exemplary sulfonium cations include triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris (3-tert-butoxyphenyl)sulfonium, (3,4-di-tert-butoxyphenyl) diphenylsulfonium, bis(3,4-di-tert-butoxyphenyl) phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 4-methylphenyldiphenylsulfonium, 4-tert-butylphenyldiphenylsulfonium, bis(4-methylphenyl)phenylsulfonium, bis(4-tert-butylphenyl)phenylsulfonium, tris(4-methylphenyl)sulfonium, tris(4-tert-butylphenyl)sulfonium, tris(phenylmethyl)sulfonium, 2-naphthyldiphenylsulfonium, dimethyl-2-naphthylsulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxopropylthiacyclopentanium, 2-oxobutylthiacyclopentanium, 2-oxo-3,3-dimethylbutylthiacyclopentanium, 2-oxo-2-phenylethylthiacyclopentanium, 4-n-butoxynaphthyl-1-thiacyclopentanium, and 2-n-butoxynaphthyl-1-thiacyclopentanium. Exemplary sulfonates include trifluoromethanesulfonate, pentafluoroethanesulfonate, heptafluoropropanesulfonate, nonafluorobutanesulfonate, dodecafluorohexanesulfonate, pentafluoroethylperfluorocyclohexanesulfonate, heptadecafluorooctanesulfonate, perfluoro-4-ethylcyclohexanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4'-toluenesulfonyloxy)benzenesulfonate, 6-(4-toluenesulfonyloxy)naphthalene-2-sulfonate, 4-(4-toluenesulfonyloxy)naphthalene-1-sulfonate, 5-(4-toluenesulfonyloxy)naphthalene-1-sulfonate, 8-(4- toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl) ethanesulfonate. Exemplary bis(substituted alkanesulfonyl)imides include bistrifluoromethanesulfonylimide, bispentafluoroethanesulfonylimide, bisheptafluoropropanesulfonylimide, and 1,3-propylenebissulfonylimide. A typical tris(substituted alkylsulfonyl)methide is tristrifluoromethylsulfonylmethide. Sulfonium salts based on combination of the foregoing examples are included.

Iodonium salts are salts of iodonium cations with sulfonates, bis(substituted alkylsulfonyl)imides and tris(substituted alkylsulfonyl)methides. Exemplary iodonium cations are aryliodonium cations including diphenyliodinium, bis(4-tert-butylphenyl)iodonium, 4-tert-butoxyphenylphenyliodonium, and 4-methoxyphenylphenyliodonium. Exemplary sulfonates include trifluoromethanesulfonate, pentafluoroethanesulfonate, heptafluoropropanesulfonate, nonafluorobutanesulfonate, dodecafluorohexanesulfonate, pentafluoroethylperfluorocyclohexanesulfonate, heptadecafluorooctanesulfonate, perfluoro-4-ethylcyclohexanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4'-toluenesulfonyloxy)benzenesulfonate, 6-(4-toluenesulfonyloxy)naphthalene-2-sulfonate, 4-(4-toluenesulfonyloxy)naphthalene-1-sulfonate, 5-(4-toluenesulfonyloxy)naphthalene-1-sulfonate, 8-(4-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl) ethanesulfonate. Exemplary bis(substituted alkylsulfonyl)imides include bistrifluoromethylsulfonylimide, bispentafluoroethylsulfonylimide, bisheptafluoropropylsulfonylimide, and 1,3-propylenebissulfonylimide. A typical tris(substituted alkylsulfonyl)methide is tristrifluoromethylsulfonylmethide. Iodonium salts based on combination of the foregoing examples are included.

Exemplary sulfonyldiazomethane compounds include bis-sulfonyldiazomethane compounds and sulfonyl-carbonyldiazomethane compounds such as bis(ethylsulfonyl)diazomethane, bis(1-methylpropylsulfonyl)diazomethane, bis(2-methylpropylsulfonyl)diazomethane, bis(1,1-dimethylethylsulfonyl)diazomethane, bis(cyclohexylsulfonyl)diazomethane, bis(perfluoroisopropylsulfonyl)diazomethane, bis(phenylsulfonyl)diazomethane, bis(4-methylphenylsulfonyl)diazomethane, bis(2,4-dimethylphenylsulfonyl)diazomethane, bis(4-acetyloxyphenylsulfonyl)diazomethane, bis(4-methanesulfonyloxyphenylsulfonyl)diazomethane, bis(4-(4-toluenesulfonyloxy)phenylsulfonyl)diazomethane, bis(2-naphthylsulfonyl)diazomethane, 4-methylphenylsulfonylbenzoyldiazomethane, tert-butylcarbonyl-4-methylphenylsulfonyldiazomethane, 2-naphthylsulfonylbenzoyldiazomethane, 4-methylphenylsulfonyl-2-naphthoyldiazomethane, methylsulfonylbenzoyldiazomethane, and tert-butoxycarbonyl-4-methylphenylsulfonyldiazomethane.

N-sulfonyloxyimide photoacid generators include combinations of imide skeletons with sulfonates. Exemplary imide skeletons are succinimide, naphthalenedicarboximide, phthalimide, cyclohexyldicarboximide, 5-norbornene-2,3-dicarboximide, and 7-oxabicyclo[2.2.1]-5-heptene-2,3-dicarboximide. Exemplary sulfonates include trifluoromethanesulfonate, pentafluoroethanesulfonate, heptafluoropropanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl) ethanesulfonate.

Benzoinsulfonate photoacid generators include benzoin tosylate, benzoin mesylate, and benzoin butanesulfonate.

Pyrogallol trisulfonate photoacid generators include pyrogallol, phloroglucin, catechol, resorcinol, and hydroquinone, in which all the hydroxyl groups are substituted by trifluoromethanesulfonate, pentafluoroethanesulfonate, heptafluoropropanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl)ethanesulfonate.

Nitrobenzyl sulfonate photoacid generators include 2,4-dinitrobenzyl sulfonate, 2-nitrobenzyl sulfonate, and 2,6-dinitrobenzyl sulfonate, with exemplary sulfonates including trifluoromethanesulfonate, pentafluoroethanesulfonate, heptafluoropropanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl) ethanesulfonate. Also useful are analogous nitrobenzyl sulfonate compounds in which the nitro group on the benzyl side is substituted by a trifluoromethyl group.

Sulfone photoacid generators include bis(phenylsulfonyl)methane, bis(4-methylphenylsulfonyl)methane, bis(2-naphthylsulfonyl)methane, 2,2-bis(phenylsulfonyl)propane, 2,2-bis(4-methylphenylsulfonyl)propane, 2,2-bis(2-naphthylsulfonyl)propane, 2-methyl-2-(p-toluenesulfonyl)propiophenone, 2-cyclohexylcarbonyl-2-(p-toluenesulfonyl)propane, and 2,4-dimethyl-2-(p-toluenesulfonyl)pentan-3-one.

Illustrative of the O-arenesulfonyloxime or O-alkanesulfonyloxime compound (oximesulfonate) are photoacid generators in the form of glyoxime derivatives, typically the compounds described in Japanese Patent No. 2,906,999 and JP-A 9-301948; photoacid generators of oximesulfonate type having a conjugated system extended via thiophene or cyclohexadiene, typically the compounds described in U.S. Pat. No. 6,004,724; oximesulfonate compounds stabilized with electron withdrawing groups such as trifluoromethyl groups, typically the compounds described in U.S. Pat. No. 6,261,738, JP-A 2000-314956, and International Publication 2004/074242; oximesulfonate compounds derived from phenylacetonitrile and substituted acetonitriles, typically the compounds described in JP-A 9-95479, JP-A 9-230588 and the references cited therein; and bisoximesulfonate compounds, typically the compounds described in JP-A 9-208554, GB 2,348,644A, and JP-A 2002-278053.

When the second photoacid generator (C) is added to the resist composition for KrF excimer laser lithography, the preferred photoacid generators are sulfonium salts, bissulfonyldiazomethanes, N-sulfonyloxydicarboximides, and oximesulfonates. Illustrative preferred photoacid generators include triphenylsulfonium p-toluenesulfonate, triphenylsulfonium camphorsulfonate, triphenylsulfonium pentafluorobenzenesulfonate, triphenylsulfonium nonafluorobutanesulfonate, triphenylsulfonium 4-(4'-toluenesulfonyloxy)benzenesulfonate, triphenylsulfonium 2,4,6-triisopropylbenzenesulfonate, 4-tert-butoxyphenyldiphenylsulfonium p-toluenesulfonate, 4-tert-butoxyphenyldiphenylsulfonium camphorsulfonate, 4-tert-butoxyphenyldiphenylsulfonium 4-(4'-toluenesulfonyl-oxy)benzenesulfonate, tris(4-methylphenyl)sulfonium camphorsulfonate, tris(4-tert-butylphenyl)sulfonium camphorsulfonate, bis(tert-butylsulfonyl)diazomethane, bis(cyclohexylsulfonyl)diazomethane, bis(2,4-dimethylphenylsulfonyl)diazomethane, bis(4-tert-butylphenylsulfonyl)diazomethane, N-camphorsulfonyloxy-5-norbornene-2,3-carboximide, N-p-toluenesulfonyloxy-5-norbornene-2,3-carboximide, (5-(10-camphorsulfonyl)oximino-5H-thiophen-2-ylidene), (2-methylphenyl)acetonitrile, 5-(4-toluenesulfonyl)oximino-5H-thiophen-2-ylidene(2-methylphenyl)acetonitrile.

In the resist composition comprising the O-propanesulfonyloxime compound as the first photoacid generator (B) according to the invention, the second photoacid generator (C) may be used in any desired amount as long as it does not compromise the effects of the O-propanesulfonyloxime compound. An appropriate amount of the second photoacid generator (C) is 0 to 10 parts, and especially 0 to 5 parts by weight among 100 parts by weight of the solids in the composition. Too high a proportion of the second photoacid generator (C) may give rise to problems of degraded resolution and foreign matter upon development and resist film peeling. The second photoacid generators may be used alone or in admixture of two or more. The transmittance of the resist film can be controlled by using a (second) photoacid generator having a low transmittance at the exposure wavelength and adjusting the amount of the photoacid generator added.

In the resist composition comprising the O-propanesulfonyloxime compound as the photoacid generator according to the invention, there may be added a compound which is decomposed with an acid to generate another acid, that is, acid-amplifier compound. For these compounds, reference should be made to J. Photopolym. Sci. and Tech., 8, 43-44, 45-46 (1995), and ibid., 9, 29-30 (1996).

Examples of the acid-amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition of the invention, an appropriate amount of the acid-amplifier compound is up to 2 parts, and especially up to 1 part by weight among 100 parts by weight of the solids in the composition. Excessive amounts of the acid-amplifier compound make diffusion control difficult, leading to degradation of resolution and pattern configuration.

Component (D)

The basic compound used as component (D) is preferably a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure and reduces substrate and environment dependence, as well as improving the exposure latitude and the pattern profile.

Examples of basic compounds include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amide derivatives, and imide derivatives.

Examples of suitable primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridine, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds having carboxyl group include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable nitrogen-containing compounds having sulfonyl group include 3-pyridinesulfonic acid and pyridinium p-toluenesulfonate. Examples of suitable nitrogen-containing compounds having hydroxyl group, nitrogen-containing compounds having hydroxyphenyl group, and alcoholic nitrogen-containing compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide.

In addition, basic compounds of the following general formula (D1) may also be included alone or in admixture.

$$N(X')_w(Y)_{3-w} \quad (D1)$$

In the formula, w is equal to 1, 2 or 3; Y is independently hydrogen or a straight, branched or cyclic alkyl group of 1 to 20 carbon atoms which may contain a hydroxyl group or ether structure; and X' is independently selected from groups of the following general formulas (X'1) to (X'3), and two or three X' may bond together to form a ring.

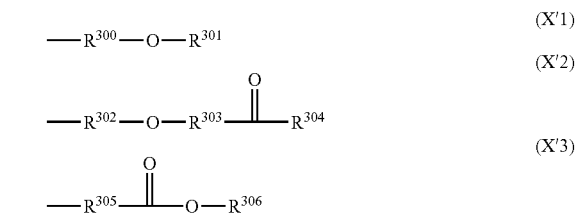

In the formulas, $R^{300}$, $R^{302}$ and $R^{305}$ are independently straight or branched alkylene groups of 1 to 4 carbon atoms; $R^{301}$, $R^{304}$ and $R^{306}$ are independently hydrogen, straight, branched or cyclic alkyl groups of 1 to 20 carbon atoms, which may contain at least one hydroxyl group, ether structure, ester structure or lactone ring; and $R^{303}$ is a single bond or a straight or branched alkylene group of 1 to 4 carbon atoms.

Illustrative examples of the basic compounds of formula (D1) include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)-ethylamine, N,N-bis(2-acetoxyethyl)-2-(tetrahydrofurfuryloxycarbonyl)-ethylamine, N,N-bis(2-hydroxyethyl)-2-[(2-oxotetrahydrofuran-3-yl)oxy-carbonyl]ethylamine, N,N-bis(2-acetoxyethyl)-2-[(2-oxotetrahydrofuran-3-yl)oxy-carbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)-ethylamine, N,N-bis(2-formyloxyethyl)-2-(2-formyloxyethoxycarbonyl)-ethylamine, N,N-bis(2-methoxyethyl)-2-(methoxycarbonyl)ethylamine, N-(2-hydroxyethyl)-bis[2-(methoxycarbonyl)ethyl]amine, N-(2- acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl)amine, tris(ethoxycarbonylmethyl)amine, N-butyl-bis(methoxycarbonylmethyl)amine, N-hexyl-bis(methoxycarbonylmethyl)amine, and β-(diethylamino)-δ-valerolactone.

Also useful are one or more of cyclic structure-bearing basic compounds having the following general formula (D2).

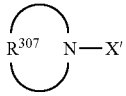
(D2)

Herein X' is as defined above, and $R^{307}$ is a straight or branched alkylene group of 2 to 20 carbon atoms which may contain one or more carbonyl groups, ether structures, ester structures or sulfide structures.

Illustrative examples of the cyclic structure-bearing basic compounds having formula (D2) include 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, and 2-methoxyethyl morpholinoacetate.

Also, one or more of cyano-bearing basic compounds having the following general formulae (D3) to (D6) may be blended.

(D3)

(D4)

(D5)

(D6)

Herein, X', $R^{307}$ and w are as defined above, and $R^{308}$ and $R^{309}$ each are independently a straight or branched alkylene group of 1 to 4 carbon atoms.

Illustrative examples of the cyano-bearing basic compounds having formulae (D3) to (D6) include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiono-nitrile, N-(2-cyanoethyl)-N-(3-hydroxy-1-propyl)-3-aminopropiono-nitrile, N-(3-acetoxy-1-propyl)-N-(2-cyanoethyl)-3-aminopropiono-nitrile, N-(2-cyanoethyl)-N-(3-formyloxy-1-propyl)-3-aminopropiono-nitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-]2-(methoxymethoxy)ethyl)aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis (2-methoxyethyl)-3-aminopropionate, cyanomethyl N,N-bis[2-(methoxymethoxy)ethyl]-3-amino-propionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-amino-propionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

The basic compounds may be used alone or in admixture of two or more. The basic compound is preferably formulated in an amount of 0 to 2 parts, and especially 0.01 to 1 part by weight, among 100 parts by weight of the solids in the resist composition. The use of more than 2 parts of the basis compound would result in too low a sensitivity.

Component (E)

Illustrative, non-limiting, examples of the organic acid derivatives (E) include phenol, cresol, catechol, resorcinol, pyrogallol, phloroglucin, bis(4-hydroxyphenyl)methane, 2,2-bis(4'-hydroxyphenyl)propane, bis(4-hydroxyphenyl)sulfone, 1,1,1-tris(4'-hydroxyphenyl)ethane, 1,1,2-tris(4'-hydroxyphenyl)ethane, hydroxybenzophenone, 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxyphenyl)valeric acid, 4-tert-butoxyphenylacetic acid, 4-(4-hydroxyphenyl)butyric acid, 3,4-dihydroxymandelic acid, and 4-hydroxymandelic acid. Of these, salicylic acid and 4,4-bis(4'-hydroxyphenyl)valeric acid are preferred. They may be used alone or in admixture of two or more.

In the resist composition of the invention, the organic acid derivative is preferably formulated in an amount of up to 5 parts, and especially up to 1 part by weight, among 100 parts by weight of the solids in the resist composition. The use of more than 5 parts of the organic acid derivative would result in too low a resolution. Depending on the combination of the other components in the resist composition, the organic acid derivative may be omitted.

Component (F)

Component (F) is an organic solvent. Illustrative, non-limiting, examples include butyl acetate, amyl acetate, cyclohexyl acetate, 3-methoxybutyl acetate, methyl ethyl ketone, methyl amyl ketone, cyclohexanone, cyclopentanone, 3-ethoxyethyl propionate, 3-ethoxymethyl propionate, 3-methoxymethyl propionate, methyl acetoacetate, ethyl acetoacetate, diacetone alcohol, methyl pyruvate, ethyl pyruvate, propylene glycol monomethyl ether, propylene glycol monoethyl ether, propylene glycol monomethyl ether propionate, propylene glycol monoethyl ether propionate, ethylene glycol monomethyl ether, ethylene glycol monoethyl ether, diethylene glycol monomethyl ether, diethylene glycol monoethyl ether, 3-methyl-3-methoxybutanol, N-methylpyrrolidone, dimethyl sulfoxide, γ-butyrolactone; propylene glycol alkyl ether acetates such as propylene glycol methyl ether acetate, propylene glycol ethyl ether acetate, propylene glycol propyl ether acetate; alkyl lactates such as methyl lactate, ethyl lactate, propyl lactate; and tetramethylene sulfone. Of these, the propylene glycol alkyl ether acetates and alkyl lactates are especially preferred. The solvents may be used alone or in admixture of two or more. An exemplary useful solvent mixture is a mixture of a propylene glycol alkyl ether acetate and an alkyl lactate.

It is noted that the alkyl groups of the propylene glycol alkyl ether acetates are preferably those of 1 to 4 carbon atoms, for example, methyl, ethyl and propyl, with methyl and ethyl being especially preferred. Since the propylene glycol alkyl ether acetates include 1,2- and 1,3-substituted ones, each includes three isomers depending on the combination of substituted positions, which may be used alone or in admixture. It is also noted that the alkyl groups of the alkyl lactates are preferably those of 1 to 4 carbon atoms, for example, methyl, ethyl and propyl, with methyl and ethyl being especially preferred.

When the propylene glycol alkyl ether acetate is used as the solvent, it preferably accounts for at least 50% by weight of the entire solvent. Also when the alkyl lactate is used as the solvent, it preferably accounts for at least 50% by weight of the entire solvent. When a mixture of propylene glycol alkyl ether acetate and alkyl lactate is used as the solvent, that mixture preferably accounts for at least 50% by weight of the entire solvent.

The solvent is preferably used in an amount of 300 to 2,000 parts by weight, especially 400 to 1,000 parts by weight, relative to 100 parts by weight of the solids in the resist composition. The solvent concentration is not limited thereto as long as a film can be formed by existing methods.

Component (G)

In one preferred embodiment, the resist composition further contains (G) a compound with a molecular weight of up to 3,000 which changes its solubility in an alkaline developer under the action of an acid, that is, a dissolution inhibitor. Typically, a compound obtained by partially or entirely substituting acid labile substituents on a phenol or carboxylic acid derivative having a molecular weight of up to 3,000, especially up to 2,500 is added as the dissolution inhibitor.

Examples of the phenol or carboxylic acid derivative having a molecular weight of up to 2,500 include bisphenol A, bisphenol H, bisphenol S, 4,4-bis(4'-hydroxyphenyl)valeric acid, tris(4-hydroxyphenyl)methane, 1,1,1-tris(4'-hydroxyphenyl)ethane, 1,1,2-tris(4'-hydroxyphenyl)ethane, phenolphthalein, and thymolphthalein. The acid labile substituents are the same as those exemplified as the acid labile groups in the polymer.

Illustrative, non-limiting, examples of the dissolution inhibitors which are useful herein include bis(4-(2'-tetrahydropyranyloxy)phenyl)methane, bis(4-(2'-tetrahydrofuranyloxy)phenyl)methane, bis(4-tert-butoxyphenyl)methane, bis(4-tert-butoxycarbonyloxyphenyl)methane, bis(4-tert-butoxycarbonylmethyloxyphenyl)methane, bis(4-(1'-ethoxyethoxy)phenyl)methane, bis(4-(1'-ethoxypropyloxy)phenyl)methane, 2,2-bis(4'-(2"-tetrahydropyranyloxy))propane, 2,2-bis(4'-(2"-tetrahydrofuranyloxy)phenyl)propane, 2,2-bis(4'-tert-butoxyphenyl)propane, 2,2-bis(4'-tert-butoxycarbonyloxyphenyl)propane, 2,2-bis(4-tert-butoxycarbonylmethyloxyphenyl)propane, 2,2-bis(4'-(1"-ethoxyethoxy)phenyl)propane, 2,2-bis(4'-(1"-ethoxypropyloxy)phenyl)propane, tert-butyl 4,4-bis(4'-(2"-tetrahydropyranyloxy)phenyl)-valerate, tert-butyl 4,4-bis(4'-(2"-tetrahydrofuranyloxy)phenyl)-valerate, tert-butyl 4,4-bis(4'-tert-butoxyphenyl)valerate, tert-butyl 4,4-bis(4-tert-butoxycarbonyloxyphenyl)valerate, tert-butyl 4,4-bis(4'-tert-butoxycarbonylmethyloxyphenyl)-valerate, tert-butyl 4,4-bis(4'-(1"-ethoxyethoxy)phenyl)valerate, tert-butyl 4,4-bis(4'-(1"-ethoxypropyloxy)phenyl)valerate, tris(4-(2'-tetrahydropyranyloxy)phenyl)methane, tris(4-(2'- tetrahydrofuranyloxy)phenyl)methane, tris(4-tert-butoxyphenyl)methane, tris(4-tert-butoxycarbonyloxyphenyl)methane, tris(4-tert-butoxycarbonyloxymethylphenyl)methane, tris(4-(1'-ethoxyethoxy)phenyl)methane, tris(4-(1'-ethoxypropyloxy) phenyl)methane, 1,1,2-tris(4'-(2''-tetrahydropyranyloxy) phenyl)ethane, 1,1,2-tris(4'-(2''-tetrahydrofuranyloxy) phenyl)ethane, 1,1,2-tris(4'-tert-butoxyphenyl)ethane, 1,1,2-tris(4'-tert-butoxycarbonyloxyphenyl)ethane, 1,1,2-tris(4'-tert-butoxycarbonylmethyloxyphenyl)ethane, 1,1,2-tris(4'-(1'-ethoxyethoxy)phenyl)ethane, and 1,1,2-tris(4'-(1'-ethoxypropyloxy)phenyl)ethane.

In the resist composition of the invention, an appropriate amount of the dissolution inhibitor is up to 20 parts, and especially up to 15 parts by weight, among 100 parts by weight of the solids in the resist composition. With more than 20 parts of the dissolution inhibitor, the resist composition becomes less heat resistant because of an increased content of monomer components.

Component (H)

In a chemically amplified negative resist composition as well, the O-propanesulfonyloxime compound of formula (1) according to the invention may be used as the photoacid generator. This composition further contains an alkali-soluble resin as component (H), examples of which are intermediates of the above-described component (A), though not limited thereto. Examples of the alkali-soluble resin include poly(p-hydroxystyrene), poly(m-hydroxystyrene), poly(4-hydroxy-2-methylstyrene), poly(4-hydroxy-3-methylstyrene), poly($\alpha$-methyl-p-hydroxystyrene), partially hydrogenated p-hydroxystyrene copolymers, p-hydroxystyrene-$\alpha$-methyl-p-hydroxystyrene copolymers, p-hydroxystyrene-$\alpha$-methylstyrene copolymers, p-hydroxystyrene-styrene copolymers, p-hydroxystyrene-m-hydroxystyrene copolymers, p-hydroxystyrene-styrene copolymers, p-hydroxystyrene-acrylic acid copolymers, p-hydroxystyrene-methacrylic acid copolymers, p-hydroxystyrene-methyl methacrylate copolymers, p-hydroxystyrene-acrylic acid-methyl methacrylate copolymers, p-hydroxystyrene-methyl acrylate copolymers, p-hydroxystyrene-methacrylic acid-methyl methacrylate copolymers, poly(methacrylic acid), poly (acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydrbxystyrene-methacrylic acid-maleimide copolymers, but are not limited to these combinations.

Preferred are poly(p-hydroxystyrene), partially hydrogenated p-hydroxystyrene copolymers, p-hydroxystyrene-styrene copolymers, p-hydroxystyrene-acrylic acid copolymers, and p-hydroxystyrene-methacrylic acid copolymers.

To impart a certain function, suitable substituent groups may be introduced into some of the phenolic hydroxyl and carboxyl groups on the foregoing polymer with protected acid labile groups. Exemplary and preferred are substituent groups for improving adhesion to the substrate, substituent groups for improving etching resistance, and especially substituent groups which are relatively stable against acid and alkali and effective for controlling such that the dissolution rate in an alkali developer of unexposed and low exposed areas of a resist film may not become too high. Illustrative, non-limiting, substituent groups include 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxolanyl, 4-methyl-2-oxo-4-oxanyl, methyl, ethyl, n-propyl, isopropyl, n-butyl, sec-butyl, acetyl, pivaloyl, adamantyl, isoboronyl, and cyclohexyl. It is also possible to introduce acid-decomposable substituent groups such as t-butoxycarbonyl and relatively acid-undecomposable substituent groups such as t-butyl and t-butoxycarbonylmethyl.

In the resist composition, the above resin (H) is blended in any desired amount, preferably of 65 to 99 parts by weight, especially 65 to 98 parts by weight among 100 parts by weight of the solids.

Component (I)

Also contained in the negative resist composition is (I) an acid crosslinker capable of forming a crosslinked structure under the action of an acid. Typical acid crosslinkers are compounds having at least two hydroxymethyl, alkoxymethyl, epoxy or vinyl ether groups in a molecule. Substituted glycoluril derivatives, urea derivatives, and hexa(methoxymethyl)melamine compounds are suitable as the acid crosslinker in the chemically amplified negative resist composition. Examples include N,N,N',N'-tetramethoxymethylurea, hexamethoxymethylmelamine, tetraalkoxymethyl-substituted glycoluril compounds such as tetrahydroxymethyl-substituted glycoluril and tetramethoxymethylglycbluril, and condensates of phenolic compounds such as substituted or unsubstituted bis(hydroxymethylphenol) compounds and bisphenol A with epichlorohydrin. Especially preferred acid crosslinkers include 1,3,5,7-tetraalkoxymethylglycolurils such as 1,3,5,7-tetramethoxymethylglycoluril, as well as 1,3,5,7-tetrahydroxymethylglycoluril, 2,6-dihydroxymethyl-p-cresol, 2,6-dihydroxymethylphenol, 2,2',6,6'-tetrahydroxymethyl-bisphenol A, 1,4-bis[2-(2-hydroxypropyl)]benzene, N,N,N', N'-tetramethoxymethylurea, and hexamethoxymethylmelamine.

An appropriate amount of the acid crosslinker is, but not limited thereto, about 1 to 20 parts, and especially about 5 to 15 parts by weight among 100 parts by weight of the solids in the resist composition. The acid crosslinkers may be used alone or in admixture of any.

Component (J)

Component (J) is an alkali-soluble compound having a molecular weight of up to 2,500. Any suitable compound may be used although a compound having at least two phenol and/or carboxyl groups is preferred. Illustrative, non-limiting, examples of the alkali-soluble compound (J) include cresol, catechol, resorcinol, pyrogallol, phloroglucin, bis(4-hydroxyphenyl)methane, 2,2-bis(4'-hydroxyphenyl)propane, bis(4-hydroxyphenyl)sulfone, 1,1,1-tris(4'-hydroxyphenyl)ethane, 1,1,2-tris(4'-hydroxyphenyl)ethane, hydroxybenzophenone, 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxyphenyl) valeric acid, 4-tert-butoxyphenylacetic acid, 4-(4-hydroxyphenyl)butyric acid, 3,4-dihydroxymandelic acid, and 4-hydroxymandelic acid. Of these, salicylic acid and 4,4-bis(4'-hydroxyphenyl)valeric acid are preferred. They may be used alone or in admixture of two or more. The alkali-soluble compound is blended in any desired amount, preferably of 0 to 20 parts by weight, especially 2 to 10 parts by weight among 100 parts by weight of the solids in the resist composition.

In the chemically amplified resist composition of the invention, there may be added such additives as surfactants for improving coating and light absorbing agents (typically, UV absorbers) for reducing diffuse reflection from the substrate.

Illustrative, non-limiting, examples of the surfactant include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (Tohkem Products Co., Ltd.), Megaface F171, F172 and F173 (Dai-Nippon Ink & Chemicals, Inc.), Fluorad FC430 and FC431 (Sumitomo 3M Co., Ltd.), Aashiguard AG710, Surflon S-381, S-382, SC101, SC102, SC103, SC104, SC105, SC106, Surfynol E1004, KH-10, KH-20, KH-30 and KH-40 (Asahi Glass Co., Ltd.); organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo Co., Ltd.). Inter alia, FC430, Surflon S-381, Surfynol E1004, KH-20 and KH-30 are preferred. These surfactants may be used alone or in admixture.

In the chemically amplified resist composition according to the invention, the surfactant is preferably formulated in an amount of up to 2 parts, and especially up to 1 part by weight, among 100 parts by weight of the solids in the resist composition.

In the chemically amplified resist composition according to the invention, UV absorbers may be added. Those UV absorbers described in JP-A 11-190904 are useful, but the invention is not limited thereto. Exemplary UV absorbers are diaryl sulfoxide derivatives such as bis(4-hydroxyphenyl) sulfoxide, bis(4-tert-butoxyphenyl) sulfoxide, bis(4-tert-butoxycarbonyloxyphenyl) sulfoxide, and bis[4-(1-ethoxyethoxy)phenyl]sulfoxide; diarylsulfone derivatives such as bis(4-hydroxyphenyl)sulfone, bis(4-tert-butoxyphenyl)sulfone, bis(4-tert-butoxycarbonyloxyphenyl)sulfone, bis[4-(1-ethoxyethoxy)phenyl]sulfone, and bis[4-(1-ethoxypropoxy)phenyl]sulfone; diazo compounds such as benzoquinonediazide, naphthoquinonediazide, anthraquinonediazide, diazofluorene, diazotetralone, and diazophenanthrone; quinonediazide group-containing compounds such as complete or partial ester compounds between naphthoquinone-1,2-diazide-5-sulfonic acid chloride and 2,3,4-trihydroxybenzophenone and complete or partial ester compounds between naphthoquinone-1,2-diazide-4-sulfonic acid chloride and 2,4,4'-trihydroxybenzophenone; tert-butyl 9-anthracenecarboxylate, tert-amyl 9-anthracenecarboxylate, tert-methoxymethyl 9-anthracenecarboxylate, tert-ethoxyethyl 9-anthracenecarboxylate, 2-tert-tetrahydropyranyl 9-anthracenecarboxylate, and 2-tert-tetrahydrofuranyl 9-anthracenecarboxylate. The UV absorber may or may not be added to the resist composition depending on the type of resist composition. An appropriate amount of UV absorber, if added, is 0 to 10 parts, more preferably 0.5 to 10 parts, most preferably 1 to 5 parts by weight, among 100 parts by weight of the base resin.

For the microfabrication of integrated circuits, any well-known lithography may be used to form a resist pattern from the chemically amplified resist composition comprising the photoacid generator of formula (1) according to the invention.

The composition is applied onto a substrate (e.g., Si, $SiO_2$, SiN, SiON, TiN, WSi, BPSG, SOG, organic anti-reflecting film, etc.) for integrated circuit microfabrication by a suitable coating technique such as spin coating, roll coating, flow coating, dip coating, spray coating or doctor coating. The coating is prebaked on a hot plate at a temperature of 60 to 150° C. for about 1 to 10 minutes, preferably 80 to 120° C. for 1 to 5 minutes. The resulting resist film is generally 0.1 to 2.0 μm thick, preferably 0.2 to 0.4 μm thick. Through a photomask having a desired pattern, the resist film is then exposed to radiation, preferably having an exposure wavelength of up to 300 nm, such as UV, deep-UV, electron beams, x-rays, excimer laser light, γ-rays and synchrotron radiation. The preferred light source is a beam from an excimer laser, especially KrF excimer laser or deep UV of 245-255 nm wavelength. The exposure dose is preferably in the range of about 1 to 200 $mJ/cm^2$, more preferably about 10 to 100 $mJ/cm^2$. The film is post-exposure baked (PEB) on a hot plate at 60 to 150° C. for 1 to 5 minutes, preferably 80 to 120° C. for 1 to 3 minutes.

Thereafter the resist film is developed with a developer in the form of an aqueous base solution, for example, 0.1 to 5%, preferably 2 to 3% aqueous solution of tetramethylammonium hydroxide (TMAH) for 0.1 to 3 minutes, preferably 0.5 to 2 minutes by conventional techniques such as dip, puddle or spray development. In this way, a desired resist pattern is formed on the substrate. It is appreciated that the resist composition of the invention is best suited for micro-patterning using such actinic radiation as deep UV with a wavelength of 254 to 193 nm, vacuum UV with a wavelength of 157 nm, electron beams, x-rays, excimer laser light, γ-rays and synchrotron radiation. With any of the above-described parameters outside the above-described range, the process may sometimes fail to produce the desired pattern.

EXAMPLE

Examples of the invention are given below by way of illustration and not by way of limitation. Mw is weight average molecular weight.

Synthesis Example 1

Synthesis of (3-(hydroxy)imino-3H-thiophen-2-ylidene)-(2-methylphenyl)-acetonitrile A solution of 128 g (2.3 mol) of potassium hydroxide in 364 g of methanol was cooled, to which 75 g (0.57 mol) of o-xylyl cyamide was added. Thereafter, a solution of 75 g (0.58 mol) of 2-nitrothiophene (purity 85%) in 218 g of methanol was added dropwise such that the temperature might not exceed 5° C. The solution was allowed to ripen for 30 minutes below 5° C., after which a solution of 551 g of glacial acetic acid in 2,200 g of water was added, and further 1,000 g of ethyl acetate added. The organic layer was separated. Ethyl acetate, 400 g, was added to the aqueous layer to effect extraction again. The organic layers were combined, washed with 200 g of saturated sodium chloride water two times, dried over anhydrous magnesium sulfate, and concentrated in vacuum, obtaining 125 g of an oily matter. It was purified by silica gel column chromatography (eluent, ethyl acetate:hexane=2:1 by volume). The elute was concentrated, followed by recrystallization from toluene, filtration and drying. There was obtained 49 g of yellow crystals (yield 35%).

The compound was analyzed by nuclear magnetic resonance (NMR) spectroscopy and infrared (IR) absorption spectroscopy, with the data shown below.

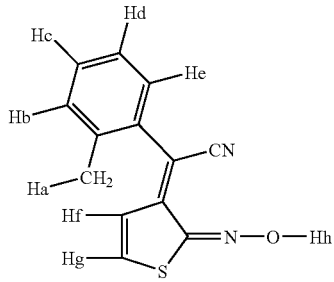

$^1$H-NMR: CDCl$_3$ (ppm)
2.37 (3H, s, Ha)
6.09-6.11 (1H, d, Hf)
6.88-6.90 (1H, d, Hg)
7.20-7.36 (4H, m, Hb, Hc, Hd, He)
9.23 (1H, s, Hh)
IR: cm$^{-1}$
3253, 3075, 3016, 2958, 2825, 2208, 1540, 1521, 1483, 1456, 1423, 1386, 1330, 1290, 1257, 1232, 1101, 1068, 1012, 991, 844, 798, 763, 734, 723, 692, 678, 644

Synthesis Example 2

Synthesis of (3-(propanesulfonyloxy)imino-3H-thiophen-2-ylidene)-(2-methylphenyl)-acetonitrile In 490 g of tetrahydrofuran were dissolved 45 g (0.19 mol) of (3-(hydroxy)imino-3H-thiophen-2-ylidene)-(2-methylphenyl)-acetonitrile in Synthesis Example 1 and 27.0 g (0.19 mol) of commercially available propanesulfonyl chloride. To the solution cooled, 20.6 g (0.20 mol) of triethylamine was added dropwise such that the temperature might not exceed 10° C. The solution was allowed to ripen for 1 hour at room temperature, after which 150 g of water and 500 g of dichloromethane were added. The organic layer was separated, and washed with 150 g of water three times. The organic layer was concentrated in vacuum. Methanol was added to the concentrate for recrystallization, followed by filtration and drying. There were obtained crude yellow crystals. The crude yellow crystals were purified by silica gel column chromatography (eluent, dichloromethane). The elute was concentrated, followed by recrystallization from methanol, filtration and drying. There was obtained 77 g of yellow crystals (yield 70%).

The compound was analyzed by NMR and IR spectroscopy, with the data shown below.

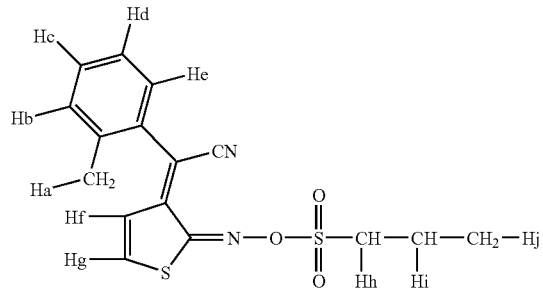

$^1$H-NMR: CDCl$_3$ (ppm)
1.11-1.16 (3H, t, Hj)
1.93-2.06 (2H, m, Hi)
2.39 (3H, s, Ha)
3.60-3.65 (2H, t, Hh)
6.19-6.20 (1H, d, Hf)
6.85-6.87 (1H, d, Hg)
7.20-7.40 (4H, m, Hb, Hc, Hd, He)
IR: cm$^{-1}$
3118, 2964, 2204, 1523, 1376, 1346, 1321, 1299, 1263, 1168, 1093, 1068, 856, 809, 771, 730, 715, 684, 617, 601, 563, 536, 522

Examples 1-9 and Comparative Examples 1-3

Resist materials were prepared in accordance with the formulation shown in Table 1. The components used are shown below.

Polymer A: 4-hydroxystyrene/4-tert-butoxystyrene copolymer having a compositional ratio of 70:30 and a Mw of 10,000

Polymer B: 4-hydroxystyrene/4-(1,1-dimethylpropoxy)-styrene copolymer having a compositional ratio of 70:30 and a Mw of 10,000

Polymer C: 4-hydroxystyrene/4-t-butoxycarbonyl-styrene copolymer having a compositional ratio of 72.5:27.5, a Mw of 15,900 and a dispersity (Mw/Mn) of 1.58

Polymer D: 4-hydroxystyrene/4-t-butoxycarbonyl-styrene copolymer having a compositional ratio of 73.0:27.0, a Mw of 10,800 and a dispersity (Mw/Mn) of 1.06

Polymer E: 4-hydroxystyrene/4-(1,1-dimethylpropoxy)-styrene/4-t-butoxycarbonylstyrene copolymer having a compositional ratio of 74.7:18.2:7.1, a Mw of 10,900 and a dispersity (Mw/Mn) of 1.05

Polymer F: 4-hydroxystyrene/4-(1,1-dimethylpropoxy)-styrene/1-ethylcyclopentyl methacrylate copolymer having a compositional ratio (molar ratio) of 75:20:5 and a Mw of 15,000

Polymer G: 4-t-butoxycarbonylstyrene/indene/4-amyloxystyrene/4-hydroxystyrene copolymer having a compositional ratio of 8.9:12.5:10.5:68.1, a Mw of 12,200 and a dispersity (Mw/Mn) of 1.81

Polymer H: indene/4-(1-methoxy-2-methylpropoxy)-styrene/4-hydroxystyrene copolymer having a compositional ratio of 10:20:70, a Mw of 14,000 and a dispersity (Mw/Mn) of 1.80

Polymer I: poly(p-hydroxystyrene) in which hydroxyl groups are protected with 30 mol % of 1-ethoxyethyl groups, having a Mw of 12,000

PAG1: compound of Synthesis Example 2
PAG2: bis(2-methyl-4-hexyloxybenzenesulfonyl)-diazomethane
PAG3: bis(2,5-dimethyl-4-hexyloxybenzene-sulfonyl)diazomethane
PAG4: triphenylsulfonium nonafluoro-1-butane-sulfonate
PAG5: (4-tert-butoxyphenyl)diphenylsulfonium 10-camphorsulfonate
PAG6: bis(cyclohexylsulfonyl)diazomethane
Basic compound A: tri-n-butylamine
Basic compound B: tris(2-methoxyethyl)amine
Organic acid derivative A: 4,4-bis(4'-hydroxyphenyl)valeric acid
Organic acid derivative B: salicylic acid
Surfactant A: FC-430 (Sumitomo 3M Co., Ltd.)
Surfactant B: Surflon S-381 (Asahi Glass Co., Ltd.)
Organic solvent A: propylene glycol methyl ether acetate
Organic solvent B: ethyl lactate The resulting resist patterns were evaluated as described below.

Resist Pattern Evaluation

The optimum exposure dose (sensitivity Eop) was the exposure dose which provided a 1:1 resolution at the top and bottom of a 0.18-μm line-and-space pattern. The minimum line width (μm) of a line-and-space pattern which was ascertained separate at this dose was the resolution of a test resist. The shape of the resolved resist pattern and the presence or absence of standing waves were determined by observing a cross section of the resist under a scanning electron microscope (SEM). A sample with no standing waves observable is judged acceptable (OK) while a sample with standing waves observable is unacceptable (NG).

The depth of focus (DOF) was determined by offsetting the focal point and judging the resist to be satisfactory when the

TABLE 1

| Composition (pbw) | Example | | | | | | | | | Comparative Example | | |
|---|---|---|---|---|---|---|---|---|---|---|---|---|
| | 1 | 2 | 3 | 4 | 5 | 6 | 7 | 8 | 9 | 1 | 2 | 3 |
| Polymer A | 80 | | | | | | | 40 | | 80 | 40 | |
| Polymer B | | 80 | | | | | | | 60 | | | |
| Polymer C | | | 80 | | | | | 40 | | | | |
| Polymer D | | | | 80 | | | | | | | | |
| Polymer E | | | | | 80 | | | | | | | |
| Polymer F | | | | | | 80 | | | | | | |
| Polymer G | | | | | | | 80 | | | | | |
| Polymer H | | | | | | | | | 20 | | 40 | |
| Polymer I | | | | | | | | | | | | 80 |
| PAG1 | 0.5 | 0.5 | 0.5 | 0.5 | 0.5 | 0.5 | 0.5 | 0.5 | 0.5 | | | |
| PAG2 | 2 | | | | | 1 | | | 1 | | | |
| PAG3 | | 2 | | | | | 1 | 1 | | 1 | | 2 |
| PAG4 | | | 2 | 2 | | 1 | | 1 | | | | |
| PAG5 | | | | | 2 | | 1 | 1 | | 1 | 2 | |
| PAG6 | | | | | | | | | | 1 | 1 | 1 |
| Basic compound A | | 0.3 | | 0.3 | 0.3 | 0.3 | | 0.3 | 0.3 | 0.15 | 0.3 | 0.3 |
| Basic compound B | 0.3 | | 0.3 | | | | 0.3 | | | 0.15 | | |
| Organic acid derivative A | | | 0.5 | | | | | 0.5 | | | | |
| Organic acid derivative B | 0.25 | | | | | | | 0.25 | | | | 0.25 |
| Surfactant A | 0.25 | 0.25 | 0.25 | 0.25 | | | | | | | 0.25 | 0.25 |
| Surfactant B | | | | | 0.25 | 0.25 | 0.25 | 0.25 | 0.25 | 0.25 | | |
| Solvent A | 385 | 385 | 385 | 280 | 385 | 385 | 385 | 385 | 385 | 280 | 382 | 385 |
| Solvent B | | | | 105 | | | | | | 105 | | |

The resist materials thus obtained were each filtered through a 0.2-μm Teflon® filter, thereby giving resist solutions. These resist solutions were spin-coated onto 8-inch silicon wafers having a silicon oxide layer of 0.02 μm thick laid thereon, so as to give a dry thickness of 0.33 μm. For the coating and subsequent baking and developing steps, a coater/developer Clean Track Act 8 by Tokyo Electron Ltd. was used.

The coated wafer was then baked on a hot plate at 110° C. for 90 seconds. The resist films were exposed to normal illumination using an excimer laser scanner NSR—S203B (Nikon Corp., NA 0.68), then baked (PEB) at 110° C. for 90 seconds, and developed with a solution of 2.38% tetramethylammonium hydroxide in water, thereby giving positive patterns (Examples 1-9 and Comparative Examples 1-3).

resist pattern shape was kept rectangular and the resist pattern film thickness was kept above 80% of that at accurate focusing.

A top loss resulting from a resist top portion being dissolved away was determined by observing a cross section of the 0.18-μm line-and-space pattern under a SEM. A sample in which the thickness of the patterned film was kept at or above 0.30 μm was judged acceptable (OK) while a sample in which the film thickness was below the level was unacceptable (NG).

The PED stability of a resist was evaluated with respect to a 0.18-μm line-and-space pattern by effecting post-exposure bake (PEB) after 24 hours of holding from exposure at the optimum dose and determining a variation of resist pattern feature size. A less variation value indicates greater PED stability.

Next, the resist materials of the formulation shown in Table 1 were similarly evaluated except that a 8-inch silicon wafer having a silicon nitride layer of 0.03 μm thick laid thereon was used instead of the 8-inch silicon wafer having a silicon oxide layer of 0.02 μm thick laid thereon. The shape of the resist 0.18-μm line-and-space pattern and the presence or absence of standing waves were determined by observing a cross section of the resist under a SEM.

The results of resist pattern evaluation are shown in Table 2.

TABLE 2

| | | Sensitivity (mJ/cm$^2$) | Resolution (μm) | Pattern profile on silicon oxide | Standing waves on silicon oxide | 0.18-μm pattern DOF (μm) | Pattern top shape | 24-hr PED dimensional stability (nm) | Pattern profile on silicon nitride | Standing waves on silicon nitride |
|---|---|---|---|---|---|---|---|---|---|---|
| Example | 1 | 40 | 0.18 | rectangular | OK | 0.6 | OK | 4 | OK | OK |
| | 2 | 25 | 0.16 | rectangular | OK | 0.8 | OK | 2 | OK | OK |
| | 3 | 32 | 0.18 | rectangular | OK | 0.6 | OK | 3 | OK | OK |
| | 4 | 30 | 0.17 | rectangular | OK | 0.7 | OK | 3 | OK | OK |
| | 5 | 23 | 0.16 | rectangular | OK | 0.8 | OK | 1 | OK | OK |
| | 6 | 22 | 0.16 | rectangular | OK | 0.8 | OK | 1 | OK | OK |
| | 7 | 35 | 0.18 | rectangular | OK | 0.6 | OK | 3 | OK | OK |
| | 8 | 35 | 0.18 | rectangular | OK | 0.6 | OK | 2 | OK | OK |
| | 9 | 22 | 0.16 | rectangular | OK | 0.8 | OK | 1 | OK | OK |
| Comparative Example | 1 | 38 | 0.18 | rectangular | NG | 0.6 | OK | 3 | OK | NG |
| | 2 | 25 | 0.18 | rounded top | NG | 0.5 | NG | 3 | NG | NG |
| | 3 | 20 | 0.18 | rounded top | NG | 0.4 | NG | −8 | NG | NG |

Other Evaluation

The solubility of resist material in a solvent mixture was examined by visual observation and in terms of clogging upon filtration.

With respect to the applicability of a resist solution, uneven coating was visually observed. Additionally, using a thickness gage Lambda Ace VM-3010 (optical interference thickness gage by Dainippon Screen Mfg. Co., Ltd.), the thickness of a resist film on an identical wafer was measured at different positions, based on which a variation from the desired coating thickness (0.6 μm) was calculated. The applicability was rated "good" when the variation was within 0.5% (that is, within 0.003 μm), "fair" when the variation was from more than 0.5% to 1%, and "poor" when the variation was more than 1%.

Storage stability was judged in terms of foreign matter precipitation or sensitivity change with the passage of time. After the resist solution was aged for 100 days at the longest, the number of particles of greater than 0.3 μm per ml of the resist solution was counted by means of a particle counter KL-20A (Rion Co., Ltd.), and the foreign matter precipitation was determined "good" when the number of particles is not more than 5. Also, the sensitivity change was rated "good" when a change with time of sensitivity (Eop) was within 5% from that immediately after preparation. Samples outside the ranges are rated "poor".

The results are shown in Table 3.

TABLE 3

| | Solubility | Applicability | Storage stability |
|---|---|---|---|
| Example 1 | good | good | good |
| Example 2 | good | good | good |
| Example 3 | good | good | good |
| Example 4 | good | good | good |
| Example 5 | good | good | good |
| Example 6 | good | good | good |
| Example 7 | good | good | good |
| Example 8 | good | good | good |
| Example 9 | good | good | good |
| Comparative Example 1 | good | good | good |
| Comparative Example 2 | good | good | good |
| Comparative Example 3 | good | good | good |

Japanese Patent Application No. 2006-164383 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A photoacid generator for use in chemically amplified resist compositions, having the formula (1):

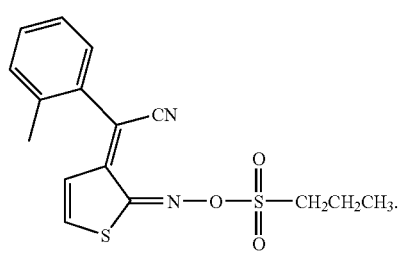

2. A chemically amplified resist composition comprising
(A) a resin which changes its solubility in an alkaline developer under the action of an acid, and
(B) the photoacid generator of claim 1.

3. The resist composition of claim 2, further comprising (C) a compound capable of generating an acid upon exposure to radiation, other than component (B).

4. The resist composition of claim 2 wherein the resin (A) has such substituent groups having C—O—C linkages that the solubility in an alkaline developer changes as a result of scission of the C—O—C linkages under the action of an acid.

5. The resist composition of claim 4 wherein the resin (A) is a polymer containing phenolic hydroxyl groups in which hydrogen atoms of the phenolic hydroxyl groups are substituted with acid labile groups of one or more types in a proportion of more than 0 mol % to 80 mol % on the average of the entire hydrogen atoms of the phenolic hydroxyl groups, the polymer having a weight average molecular weight of 3,000 to 100,000.

6. The resist composition of claim 5 wherein the resin (A) is a polymer comprising recurring units of the following general formula (2a):

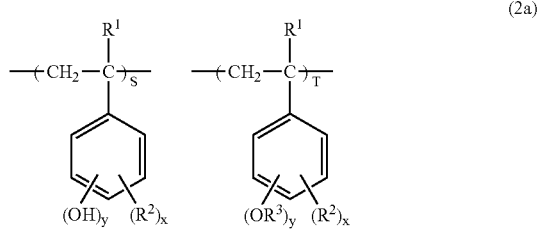

wherein $R^1$ is hydrogen or methyl, $R^2$ is a straight, branched or cyclic alkyl group of 1 to 8 carbon atoms, x is 0 or a positive integer, y is a positive integer, satisfying $x+y \leq 5$, $R^3$ is an acid labile group, S and T are positive integers, satisfying $0 < T/(S+T) \leq 0.8$,
wherein the polymer contains units in which hydrogen atoms of phenolic hydroxyl groups are partially substituted with acid labile groups of one or more types, a proportion of the acid labile group-bearing units is on the average from more than 0 mol % to 80 mol % based on the entire polymer, and the polymer has a weight average molecular weight of 3,000 to 100,000.

7. The resist composition of claim 5 wherein the resin (A) is a polymer comprising recurring units of the following general formula (2a'):

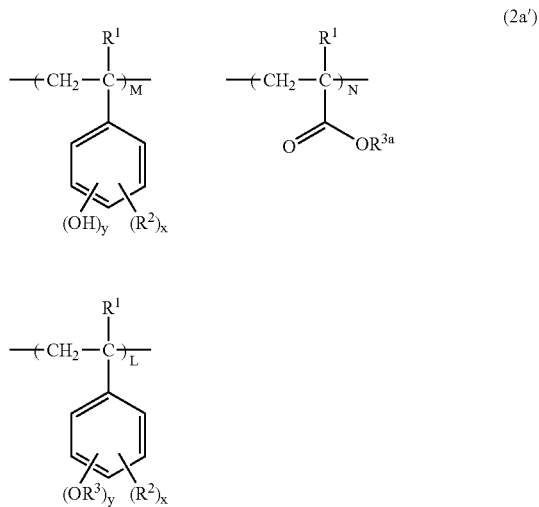

wherein $R^1$ is hydrogen or methyl, $R^2$ is a straight, branched or cyclic alkyl group of 1 to 8 carbon atoms, $R^3$ is an acid labile group, $R^{3a}$ is hydrogen or an acid labile group, at least some of $R^{3a}$ being acid labile groups, x is 0 or a positive integer, y is a positive integer, satisfying $x+y \leq 5$, M and N are positive integers, L is 0 or a positive integer, satisfying $0 < N/(M+N+L) \leq 0.5$ and $0 < (N+L)/(M+N+L) \leq 0.8$,
wherein the polymer contains on the average from more than 0 mol % to 50 mol % of those units derived from acrylate and methacrylate, and also contains on the average from more than 0 mol % to 80 mol % of acid labile group-bearing units, based on the entire polymer, and the polymer has a weight average molecular weight of 3,000 to 100,000.

8. The resist composition of claim 5 wherein the resin (A) is a polymer comprising recurring units of the following general formula (2a"):

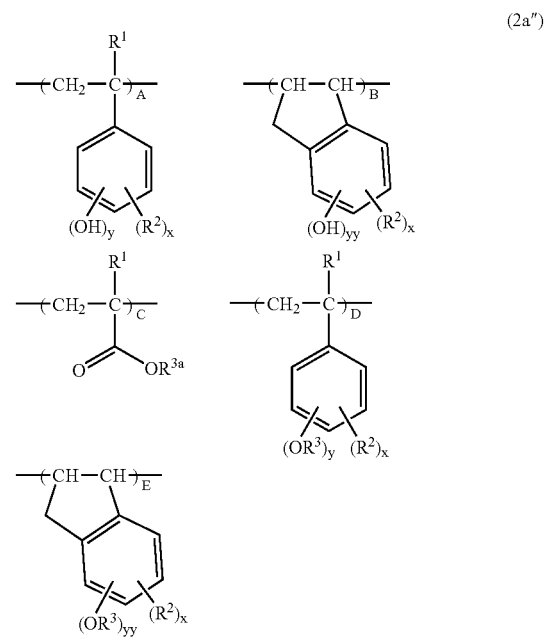

wherein $R^1$ is hydrogen or methyl, $R^2$ is a straight, branched or cyclic alkyl group of 1 to 8 carbon atoms, $R^3$ is an acid labile group, $R^{3a}$ is hydrogen or an acid labile group, at least some of $R^{3a}$ being acid labile groups, x is 0 or a positive integer, y is a positive integer, satisfying $x+y \leq 5$, yy is 0 or a positive integer, satisfying $x+yy \leq 4$, A and B are positive integers, C, D and E each are 0 or a positive integer, satisfying $0 < (B+E)/(A+B+C+D+E) \leq 0.5$ and $0 < (C+D+E)/(A+B+C+D+E) \leq 0.8$,
wherein the polymer contains on the average from more than 0 mol % to 50 mol % of those units derived from indene and/or substituted indene, and also contains on the average from more than 0 mol % to 80 mol % of acid labile group-bearing units, based on the entire polymer, and the polymer has a weight average molecular weight of 3,000 to 100,000.

9. The resist composition of claim 5 wherein the resin (A) is a polymer comprising recurring units of the following general formula (2a'''):

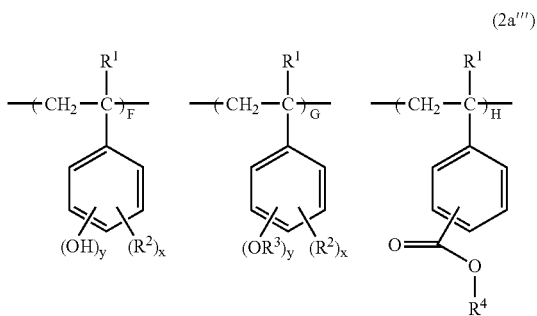

(2a''')

wherein $R^1$ is hydrogen or methyl, $R^2$ is a straight, branched or cyclic alkyl group of 1 to 8 carbon atoms, $R^3$ is an acid labile group, $R^4$ is a tertiary alkyl group of 4 to 20 carbon atoms, x is 0 or a positive integer, y is a positive integer, satisfying $x+y \leq 5$, F and H are positive integers, G is 0 or a positive integer, satisfying $0 < H/(F+G+H) \leq 0.5$ and $0 < (G+H)/(F+G+H) \leq 0.8$, wherein the polymer contains on the average from more than 0 mol % to 50 mol % of those units derived from tertiary alkoxycarbonylstyrene, and also contains on the average from more than 0 mol % to 80 mol % of acid labile group-bearing units, based on the entire polymer, and the polymer has a weight average molecular weight of 3,000 to 100,000.

10. The resist composition of claim 4 wherein the acid labile group is selected from the class consisting of groups of the following general formulae (5) and (6) and tertiary alkyl groups of 4 to 20 carbon atoms,

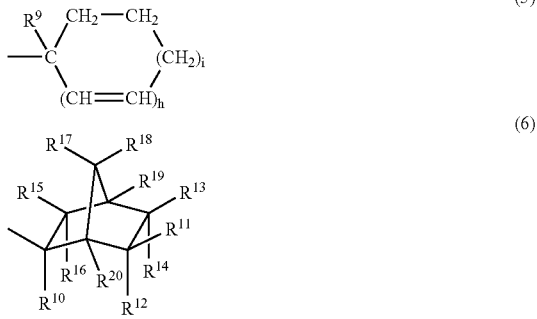

wherein $R^9$ is a straight, branched or cyclic alkyl group of 1 to 8 carbon atoms or an aryl group of 6 to 20 carbon atoms which may be substituted, h is 0 or 1, i is 0, 1, 2 or 3, satisfying 2h+i=2 or 3, $R^{10}$ is a straight, branched or cyclic alkyl group of 1 to 8 carbon atoms or an aryl group of 6 to 20 carbon atoms which may be substituted, $R^{11}$ to $R^{20}$ are each independently hydrogen or a monovalent hydrocarbon group of 1 to 15 carbon atoms which may contain a heteroatom, $R^{11}$ to $R^{20}$, taken together, may form a ring, each of $R^{11}$ to $R^{20}$ is a divalent hydrocarbon group of 1 to 15 carbon atoms which may contain a heteroatom when they form a ring, or two of $R^{11}$ to $R^{20}$ which are attached to adjoining carbon atoms may bond together directly to form a double bond.

11. The resist composition of claim 2, further comprising (D) a basic compound.

12. The resist composition of claim 2, further comprising (E) an organic acid derivative.

13. The resist composition of claim 2, further comprising (F) an organic solvent which is a propylene glycol alkyl ether acetate, an alkyl lactate or a mixture thereof.

14. A process for forming a pattern, comprising the steps of:

(i) applying the resist composition of claim 2 onto a substrate to form a coating, (ii) heat treating the coating and exposing the coating to high energy radiation with a wavelength of up to 300 nm or electron beam through a photomask, (iii) optionally heat treating the exposed coating, and developing the coating with a developer.

15. The process of claim 14, wherein said substrate is an inorganic substrate.

16. The process of claim 15, wherein the coating of the resist composition on the inorganic substrate has a thickness equal to or less than 0.4 μm.

17. A chemically amplified positive resist composition comprising (A) a resin which changes its solubility in an alkaline developer under the action of an acid, and (B) the photoacid generator of claim 1.

\* \* \* \* \*